(12) United States Patent
Mangrum et al.

(10) Patent No.: US 7,896,823 B2
(45) Date of Patent: Mar. 1, 2011

(54) METHOD AND APPARATUS FOR TREATING WOUND USING NEGATIVE PRESSURE THERAPY

(75) Inventors: Shane Mangrum, Ammon, ID (US); Daniel Burnett, San Francisco, CA (US)

(73) Assignee: TheraNova, LLC, San Francisco, CA (US)

( * ) Notice: Subject to any disclaimer, the term of this patent is extended or adjusted under 35 U.S.C. 154(b) by 0 days.

(21) Appl. No.: 11/332,756

(22) Filed: Jan. 17, 2006

(65) Prior Publication Data

US 2007/0167884 A1   Jul. 19, 2007

(51) Int. Cl.
*A61H 7/00* (2006.01)
*A61H 23/00* (2006.01)
*A61F 13/06* (2006.01)
*A61F 13/66* (2006.01)

(52) U.S. Cl. .............................. 601/9; 601/10; 601/11; 601/152; 602/56; 602/75

(58) Field of Classification Search ............... 601/6–14, 601/148–152; 604/293, 315, 316; 482/78; 602/53, 58, 75–77
See application file for complete search history.

(56) References Cited

U.S. PATENT DOCUMENTS

| | | | |
|---|---|---|---|
| 4,421,109 A * | 12/1983 | Thornton ..................... | 601/35 |
| 4,702,232 A | 10/1987 | Gardner et al. | |
| 4,841,956 A | 6/1989 | Gardner et al. | |
| 5,263,473 A | 11/1993 | McWhorter | |
| 5,514,079 A | 5/1996 | Dillon | |
| 5,549,709 A | 8/1996 | Caspers | |
| 5,657,475 A | 8/1997 | Gillespie | |
| 5,897,518 A | 4/1999 | Shaw | |
| 5,909,696 A | 6/1999 | Reinhardt | |
| 6,049,852 A | 4/2000 | Oba | |

(Continued)

FOREIGN PATENT DOCUMENTS

EP   0864983   9/1998

(Continued)

*Primary Examiner*—Danton DeMille
(74) *Attorney, Agent, or Firm*—Levine Bagade Han LLP

(57) ABSTRACT

Devices that employ external compression stocking-type garments in the treatment of edema, chronic wounds, deep venous thrombosis prevention or claudication all share a number of significant limitations. These include the frequent need for custom fitting to assure an appropriate fit, vigilant maintenance to assure a continued "good fit," limited compliance with proper use by patients and difficulty of application. There is a large body of evidence demonstrating that patients often decline to wear the compressive stockings as prescribed or in the form that would be most beneficial because they find these devices to be difficult to put on and take off.

Building on the limitations of existing therapies, and distilled lessons learned from the field of prosthetics and wound healing, the present invention employs vacuum-assisted negative pressure to provide compression and help pump fluid from the tissues of affected limbs. The device is embodied in the form of a flexible stocking-like garment that will utilize a pumping mechanism to generate negative pressure around the limb and thus create vacuum compression that will mobilize fluid in a limb and increase venous return to the heart. Through the use of a circumferential wrap, the present invention provides a major advance in both the distribution of vacuum and the securing of the device over the limb.

21 Claims, 15 Drawing Sheets

U.S. PATENT DOCUMENTS

| | | |
|---|---|---|
| 6,135,116 A | 10/2000 | Vogel et al. |
| 6,192,455 B1 | 2/2001 | Bogin |
| 6,551,280 B1 | 4/2003 | Knighton et al. |
| 6,589,194 B1 | 7/2003 | Calderon et al. |
| 6,613,953 B1 * | 9/2003 | Altura .......................... 602/43 |
| 6,752,794 B2 | 6/2004 | Lockwood et al. |
| 7,214,202 B1 | 5/2007 | Vogel et al. |
| 2003/0032904 A1 * | 2/2003 | Egger ......................... 601/151 |
| 2003/0171703 A1 * | 9/2003 | Grim et al. .................. 601/152 |
| 2003/0199800 A1 * | 10/2003 | Levin ........................... 602/43 |
| 2003/0216672 A1 * | 11/2003 | Rastegar et al. ................. 601/9 |
| 2004/0073151 A1 * | 4/2004 | Weston ........................ 602/41 |
| 2006/0287621 A1 | 12/2006 | Atkinson et al. |

FOREIGN PATENT DOCUMENTS

| | | |
|---|---|---|
| GB | 2195255 A * | 4/1988 |
| SU | 1491509 A1 * | 7/1989 |

* cited by examiner

Calf-only embodiment

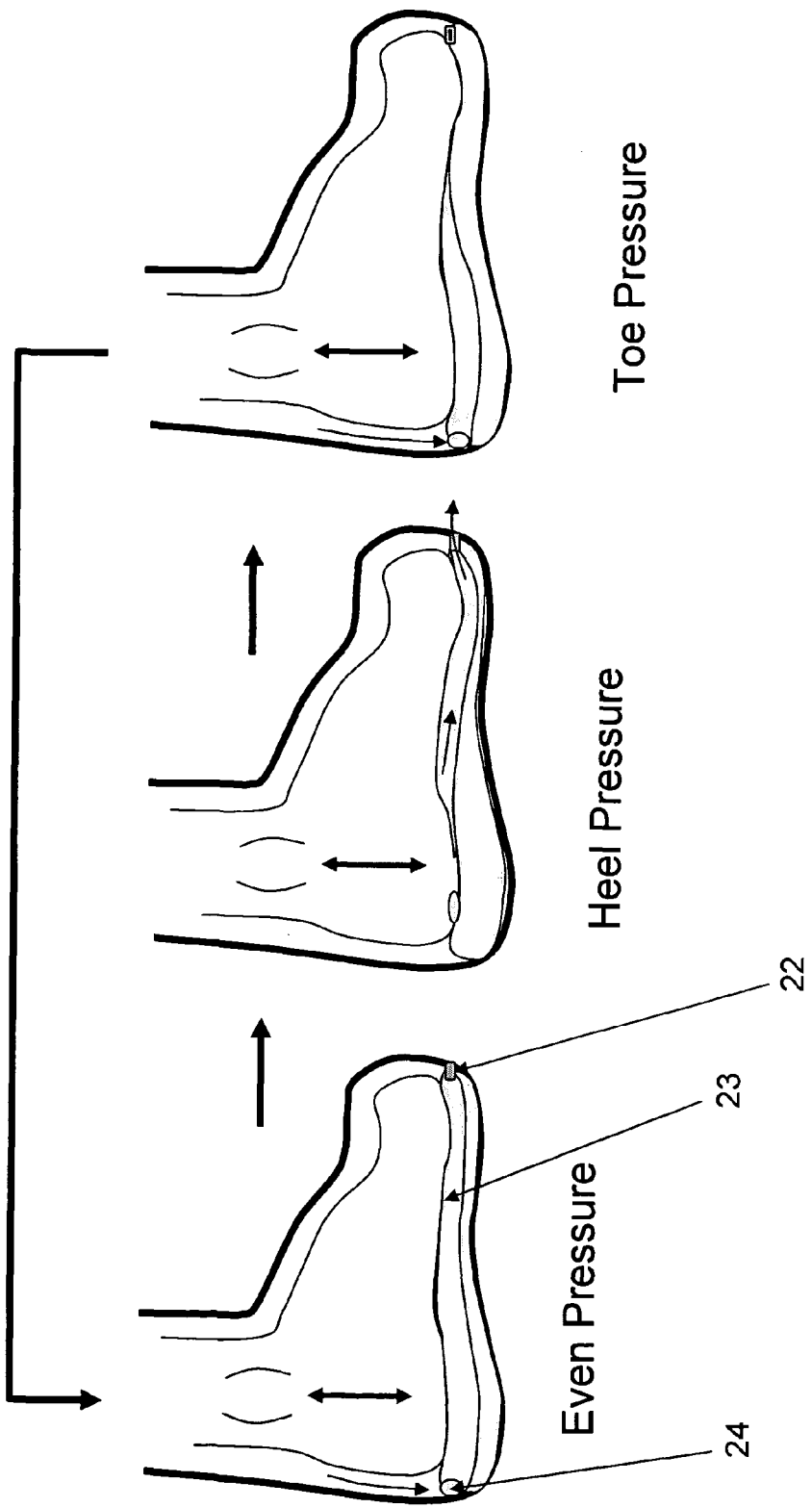

METHOD AND APPARATUS FOR TREATING WOUND USING NEGATIVE PRESSURE THERAPY

CROSS-REFERENCES TO RELATED APPLICATIONS

This application claims priority to U.S. Provisional Patent Application Ser. No. 60/643,145, filed Jan. 12$^{th}$, 2005. The relevant disclosure of the application cited in this paragraph is hereby incorporated by reference.

BACKGROUND OF THE INVENTION

The present invention relates to the field of medical devices, in particular therapeutic intervention devices for the reduction of edema and improvement of venous return to the heart with applications in the field of medicine.

Prior to the present invention, various compression devices have been known in the art for applying compressive pressure to a patient's limbs in order to increase blood flow and return of fluid from a limb.

These compression devices take a number of different forms, including:

1) The SCD (trademark of The Kendall Company), a sequential compression device that provides intermittent pulses of compressed air that sequentially inflate multiple chambers in a sleeve, beginning at the ankle and moving up the leg. This results in a wave-like milking action that empties the veins and results in greatly increased peak blood flow velocity, thus providing a non-invasive method of prophylaxis to reduce the incidence of deep vein thrombosis (DVT). Patients with edema (swelling of the extremity) can develop tissue breakdown (venous stasis ulcer). It has also been shown that pneumatic compression can be highly effective in the treatment of edema and venous ulcers.

2) Non-elastic therapeutic compression band by band, with the user capable of tightening the compression bands to control the non-elastic pressure. This form of cyclical or sequential compression of limbs improves blood fluid returns for reducing edema and can improve healing.

3) Devices that are intended to apply and remove pressure from at least a portion of the patient's extremity. For example, a patient's legs may be enclosed in air bags that may be inflated to apply pressure on the leg and deflated to remove pressure from the leg. Synchronous application of pressure on an extremity can enhance the flow of blood into the extremity, as well as enhancing the pumping of blood through the heart.

4) They function by applying pneumatic compression sequentially and in gradient levels from ankle to thigh for a predetermined time, e.g. 15 seconds, followed by a period of time, e.g. 45 seconds, when no pressure is applied. The particular time period selected is chosen to be optimum for pushing venous blood out of the leg (during the compression cycle) and to allow arterial blood to refill the leg (during the decompression interval).

Evidence suggests that it may also be advantageous to apply pneumatic compression to the foot to provide significant venous blood movement therefrom. For example, U.S. Pat. No. 4,702,232 and a division thereof, U.S. Pat. No. 4,841,956, of Arthur M. N. Gardner and Roger H. Fox relate to a device for inducing venous-return flow, which device is intended for use on an impaired human leg. In accordance with the teachings of these patents, the cyclical succession of venous pump action which would occur in normal walking is achieved by involuntarily or artificially activating a foot pump followed by artificially induced separate transient operation of a proximal calf pump and then an artificially induced separate operation of a distal calf pump. As disclosed, the pump actions are achieved by providing inflatable bags or cuffs around the foot and upper and lower calf regions, the inflatable cuffs being separately connected by tubes to a fluid pressure supply means. Each cuff is inflated and then deflated before the next cuff is inflated. Moreover, the cuffs are not inflated sequentially from distal to proximal, e.g. the sequence disclosed in the patent of foot pump, proximal calf pump and then distal calf pump which procedure does not encourage an effective pumping of blood from the leg.

In a related area of intervention, devices for prosthetic limbs have been developed to create hypobarically controlled artificial limbs for amputees and methods for preventing loss of residual limb volume due to weight-bearing pressures. An amputee is a person who has lost part of an extremity or limb such as a leg or arm that commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Devices have been developed to employ negative pressure in a closed chamber in the form of a socket is donned by pulling in with a stocking, pulling the stocking out of the socket and then closing the opening with a valve. This creates a seal at the bottom and the stump is held into the socket by the hypobaric seal.

Older appliances that employed negative pressure involved an open-ended socket, meaning there was an air chamber in the bottom of the socket. These did not work particularly well because they would cause swelling of the residual limb into the chamber created by the negative draw of suspending the weight of the leg and being under a confined area. This would lead to significance edema that would be severe enough to cause stump breakdown and drainage. It was later discovered that total contact was essential between the residual limb and the socket and once you had total contact the weight was distributed evenly or the suspension was distributed over the whole surface of the limb rather than just over the open chamber portion of the socket.

The human body as a whole is under approximately one atmosphere of pressure at sea level. It keeps and maintains a normal fluid appliance throughout the body. When an amputee dons prosthesis and begins taking the pressures of transmitting the weight of the body through the surface area of the residual limb to the bone, there is increased pressure on the residual limb equal to one atmosphere plus whatever additional pressures are created by weight bearing. This increased pressure causes the eventual loss of fluids within the residual limb to the larger portion of the body that is under less pressure. This loss of fluids causes the volume of the residual limb to decrease during the day. It varies from amputee to amputee, but it is a constant among all amputees, the more "fleshy", and the softer the residual limb, the more volume fluctuation there will be. The greater the weight and the smaller the surface area, the greater the pressures will be and the more "swings" there will be in fluids. In the past, the amputee had to compensate for this volume decrease by removing the artificial limb and donning additional stump stockings to make up for the decreased residual limb volume.

It has been found that it is essentially impossible to maintain a perfect, airtight seal between the residual limb and the sockets disclosed in U.S. Pat. No. 5,549,709, with the result that slow air leakage into the sockets diminishes the vacuum in the sockets. With the reduction in vacuum, the beneficial effects of the vacuum also slowly diminish. Consequently, there is a need for a means for maintaining the vacuum in the socket cavity in the presence of some air leakage past the seal.

A related device in U.S. Pat. No. 6,551,280 has described using vacuum assisted compression to provide support or pressure to tissue for wound healing. Lockwood et al. in U.S. Pat. No. 6,752,794 describe a similar device for the delivery of negative pressure to a wound for the purpose of wound healing. These devices are intended to contain a material that is capable of being contracted from its relaxed state to an evacuated state. The material applies pressure to the tissue of a patient when the material is in its relaxed state. Reduction of pressure by application of a vacuum results in a contracted state of the device, so that the device can be applied or delivered to a patient. Release of vacuum results in a return to the relaxed state, thus providing a maximum desirable pressure to tissue and avoiding the possibility of over-pressure that can result in tissue damage or necrosis. The description of these devices does not contemplate the use of self-powered creation and maintenance of negative pressure for edema control with ambulation. Nor does the descriptions, or any other in prior art, contemplate the use of circumferentially applied vacuum which will be crucial to the simultaneous treatment of fluid accumulations (i.e. leg edema) and skin wounds as found in both diabetes and chronic venous insufficiency.

Additionally, Vogel et al. in U.S. Pat. No. 6,135,116 contemplated a method and apparatus for providing concurrent applications of intermittent pneumatic compression therapy and vacuum assisted closure for the treatment of wounds. This patent describes the use of "a wound dressing for introduction of a negative pressure into a wound on a patient's foot and a foot wrap for application of positive, compressive forces to substantially all of the patients foot." While this patent references the use of a "wrap" the authors very specifically describe a wrap that is akin to existing intermittent positive pressure compression devices. The novelty of the patent relates, then, to the combination of these treatments. Significantly, the authors do not contemplate the use of a wrap for the delivery of negative pressure compression to an entire foot or limb.

The limitations of existing delivery systems for negative pressure wound therapy are significant and are well described in the medical literature. The Vacuum-Assisted Closure (VAC) device employs the application of foam and layers of dressing locally over a wound surface. This and related devices are limited in that: 1) Use generally requires that patients and families be willing to sleep, ambulate, and rest during the day with the device in place, 2) Weight-bearing while using the VAC is generally considered to be dangerous to patient, 3) Nearly 20% of individuals with smaller forefoot or midfoot wounds fail VAC treatment, and 4) Applications of the VAC system are not intended for small wounds or for the prevention of skin wounds. In addition, VAC is applied locally and due to the complex layering of foam and dressing of the wound, has not been applied circumferentially as is the case with the present invention.

To our knowledge, the use of a device that employs total contact with a non-amputated limb by creating and maintaining (through the use of mobility and weight bearing) a negative pressure vacuum for the control of edema has not been contemplated in the prior art. Devices have utilized positive pressure compression in various forms to facilitate the return of interstitial fluid (or edema) from limbs to the heart. Other devices have been designed to use a negative pressure vacuum to improve swelling, protect skin, and provide a means for suspension in amputated limbs.

In addition, the use of a circumferential wrap for a limb in the delivery of negative pressure for the purposes of wound healing/prevention/edema control has not been contemplated in the prior art.

The innovation of present invention involves the use of a flexible stocking-type device that is employed circumferentially around a limb and employs the creation and maintenance of negative pressure to reduce edema, improve venous return, and help protect skin.

REVIEW OF THE PRIOR ART

U.S. Pat. No. 5,263,473 describes a compression device and method for applying compressive pressure against a patient's limb in periodic compression cycles, wherein an elongated sleeve having a plurality of inflatable chambers is placed over the foot and a portion of the leg, the chambers being sequentially inflated starting with the foot and then form a distal portion of the leg toward a proximal portion of the leg relative to the heart until all of the chambers are inflated.

U.S. Pat. No. 5,897,518 describes a foot and ankle-therapeutic compression device in which a pair of foot and ankle compression bands are tightened and anchored in tightened condition by VELCRO hook and loop surfaces.

U.S. Pat. No. 6,589,194 describes a self-powered compression device of the present invention permits the wearer of a plurality of inflatable pockets that form a sleeve around the limb to apply a controlled level of circular positive pressure compression to the limb. The self-powered appliance comprises inflatable or pneumatic sleeves that wrap around the limb adopting the wearer's shape of the limb. Energy is generated by the wearer's muscle action, weight bearing gravity force and constant transfer of body weight during walking, moving or flexing of the limbs. The energy generated is transmitted to the air or liquid inflated sleeves or pockets that are installed to surround the limb. As a result of the cyclical and sequential movement of the pockets from the lower portion of the limb towards its upper portion, vector forces are generated. The resulting positive pressure compression preserves the venous reflex and aids venous flow back from the foot in the direction of the heart. While this device has taken the step to incorporate self-powered compression into the design of this appliance, the generation of negative pressure vacuum compression is not contemplated.

U.S. Pat. No. 5,514,079 a method for promoting the circulation of blood through a patient's extremity. In one aspect of the invention an inflatable enclosure, such as an air bag, is applied to an extremity (e.g., leg), so that upon inflation and deflation of the air bag, the extremity is alternately compressed and decompressed. Compression and decompression of the extremity is regulated by sensing the QRS complex in the heart cycle of the patient, computing an average time period between a selected number of successive QRS complexes, and initiating a timing cycle for compressing and decompressing the extremity.

SUMMARY OF THE INVENTION

The present invention creates and maintains negative pressure vacuum via an active pump mechanism or a self-powered pump (through the use of mobility and weight bearing) for the control of edema and/or acceleration of healing of limb wounds. Devices have utilized positive pressure compression in various forms to facilitate the return of interstitial fluid (or edema) from limbs to the heart, but devices have not been contemplated, prior to this invention, to provide circumferential vacuum therapy to a non-amputated limb. The innovation of present invention involves the use of a flexible stocking-type device that employs the creation and maintenance of negative pressure to reduce edema, improve venous return, and help protect skin.

The Dynamic Vacuum Compression Appliance consists of a sealed region, and a vacuum generating mechanism. The sealed region can be composed of urethane, silicone or any flexible material that is able to form a tubular shell capable of forming an air seal and surrounding some or all of a limb. The sealed region can be of sufficient length to cover all or part of the leg. The sealed region contains a band, e.g. an elastic or Velcro band, which can provide a relatively airtight seal to allow for vacuum generation in the leg. The sealed region may optionally contain longitudinal air support channels to allow for the transmission of vacuum from the vacuum pump to the top of the garment in a reliable manner avoiding air pockets. Alternatively, the sealed region may incorporate a pressure-sensitive or open-air influx valve. This air influx valve can allow for the development of pressure gradients in the leg or the slow-release of vacuum with a decline in the rate of vacuum pump activation. The development of pressure gradients can also be achieved through the use of air levels incorporated into the garment. These air levels can provide air pockets with variable access to vacuum, either using pressure-sensitive valves or simple smaller diameter higher resistance tubing such that the vacuum provided at increasing elevation is less than that in the inferior air level. This inter-level flow restriction feature will allow for the "milking of the leg" with activation of the vacuum pump. The air levels can also be used in combination with the air influx valve to provide a dynamic pressure gradient throughout the limb.

The vacuum generating mechanism can be incorporated into an insole-like device designed to be placed inside of standard footwear. This component will incorporate a resilient air chamber and two valves or flow restrictors (such as smaller diameter tubing) to channel air out of the garment upon compression of the air chamber by the foot and to allow air to enter the air chamber from the garment with recoil of the air chamber. The recoil and compliance of the air chamber can be tailored such that it will not recoil once a certain vacuum has been established, thus ensuring that the correct negative pressure is achieved. This appliance will thus employ the force generated during normal standing and walking to actively generate vaccum forces and allow air to be evacuated through a one-way check valve. As the negative pressure builds within the stocking, the garment surfaces will draw in around the skin to generate compression for the application of controlled pressure to the limb. This generated compression will then support the superficial venous appliance, helping to reduce edema and aid venous return.

The vacuum generating mechanism can be incorporated into the base of the garment and can be shaped like a standard shoe insert/arch support. It can attach to the stocking garment, and can fit neatly into a standard shoe, for example. The use of the device will involve simply donning the stocking garment over the intended limb. A tight seal will be created at the top of the garment. Once slipped into a shoe, the vacuum pump and valve interface will begin to generate negative pressure within the stocking and gradually provide appropriate compression to the limb. Because the negative pressure does the actual work of generating compression on a limb, the stocking garments will be significantly easier to put on and take off than existing compression garments or bandages. Alternatively, the garment will form a partial seal such that with frequent compression of the vacuum will provide strong suction that will gradually subside once the frequency of pump application is reduced. This partial seal could also be used to ensure that the vacuum generated at the top of the garment is less than that generated at the inferior portions, thus "milking" the leg.

In an alternative embodiment, the vacuum generating mechanism can be incorporated into the body of a shoe. With this embodiment, the limb compression garment can be coupled to the vacuum generating mechanism by inserting the limb with the garment in place into the shoe.

In an alternative embodiment, the vacuum generating mechanism can be incorporated into a boot (e.g. walking or post-surgical boot). With this embodiment, the air compliant chamber, valves, tubing, and other components could be built into the structure of the boot into which the compression garment would fit. This embodiment would facilitate the accommodation of limbs of various sizes, wounds of various types, and would obviate the need for designing special shoes to interface with the compression garment.

In an alternative embodiment, the limb compression garment can be fit to the upper extremity. This embodiment will allow for the treatment of lymphedema or other conditions associated with swelling of the upper extremity. In this embodiment, the vacuum generating mechanism could be designed to fit in the palm of the hand, on a weight-bearing surface of the upper extremity.

In an alternative embodiment, the device could be powered by the repeated flexion and extension of any joint or by any bodily motion. Additionally, the device could be powered by the motion of a transport vehicle (e.g. wheelchair, walker, scooter, etc.). In this embodiment, the vacuum generating source may be powered by the kinetic motion of the transport vehicle.

In an alternative embodiment, the device could be powered by a pump as a primary or complementary source of vacuum generation. The pump could be driven by any motion of the body or also by an external power source.

The competitive advantages of the Dynamic Vacuum Compression Appliance include: 1) Improved patient convenience and ease of use, 2) Improved skin protection and care of skin, and 3) Reduction of healthcare costs with the prevention of complications (such as venous ulcers) and decreased requirement for custom fitting of compression garments.

BRIEF DESCRIPTION OF THE DRAWINGS

FIG. 15 is a perspective view of one embodiment of the device employing a single valve and utilizing the natural pattern of plantar compression to generate vacuum

DETAILED DESCRIPTION OF THE DRAWINGS

The invention is susceptible to many and various embodiments; those embodiments described below should not be interpreted as restrictive, but rather as merely illustrative of the invention.

Figure 1:
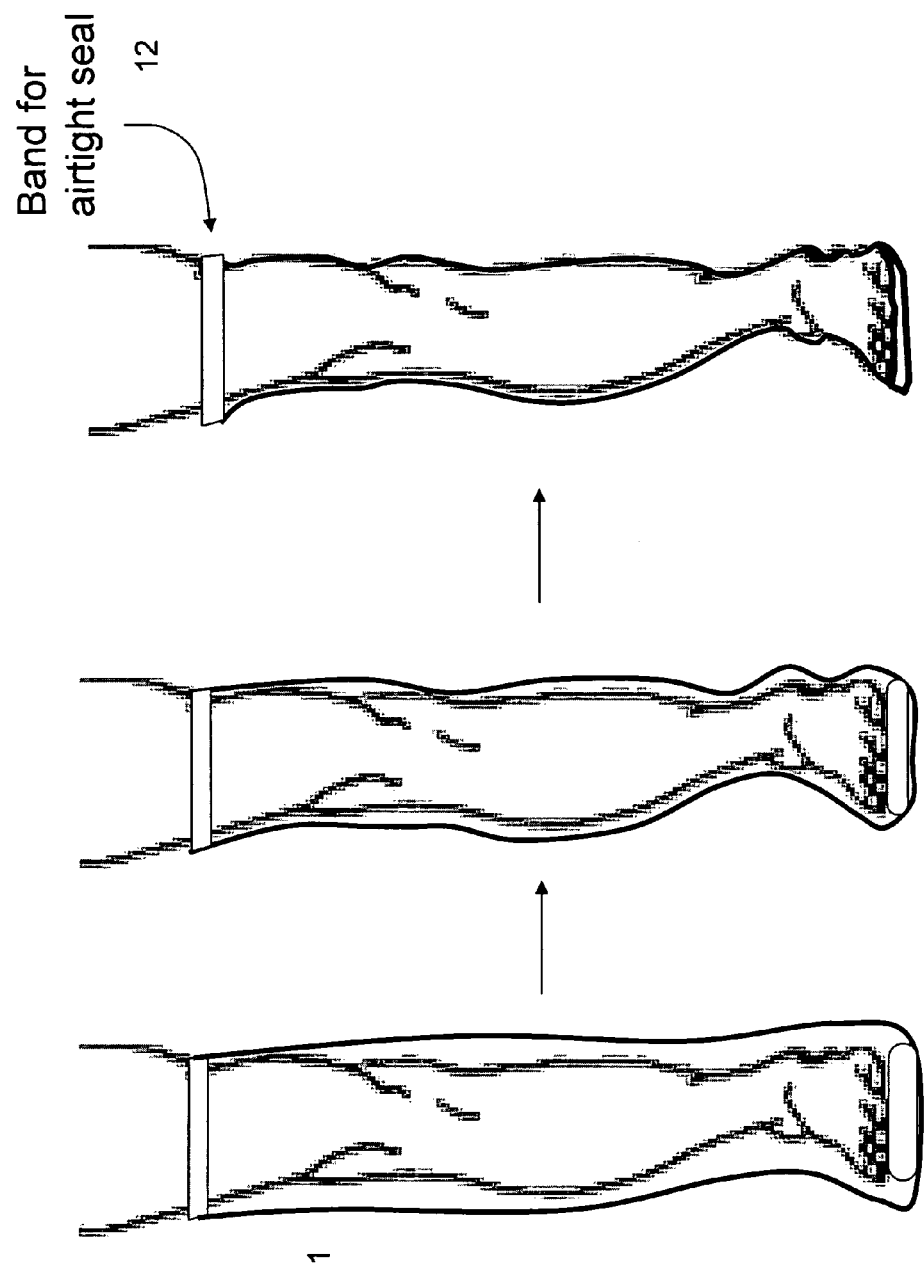
FIG. 1 is a perspective view of a Dynamic Vacuum Compression Appliance configured in accordance with one embodiment of the present invention.

As illustrated in FIG. 1, one embodiment of the present invention provides a Dynamic Vacuum Compression Appliance 1 that creates and maintains a self-powered negative pressure vacuum for the control of edema, improvement of venous return, and protection of skin. As the negative pressure builds within the stocking (illustrated in FIG. 1), the garment surfaces will draw in around the skin to generate compression for the application of controlled pressure to the limb.

Figure 2:
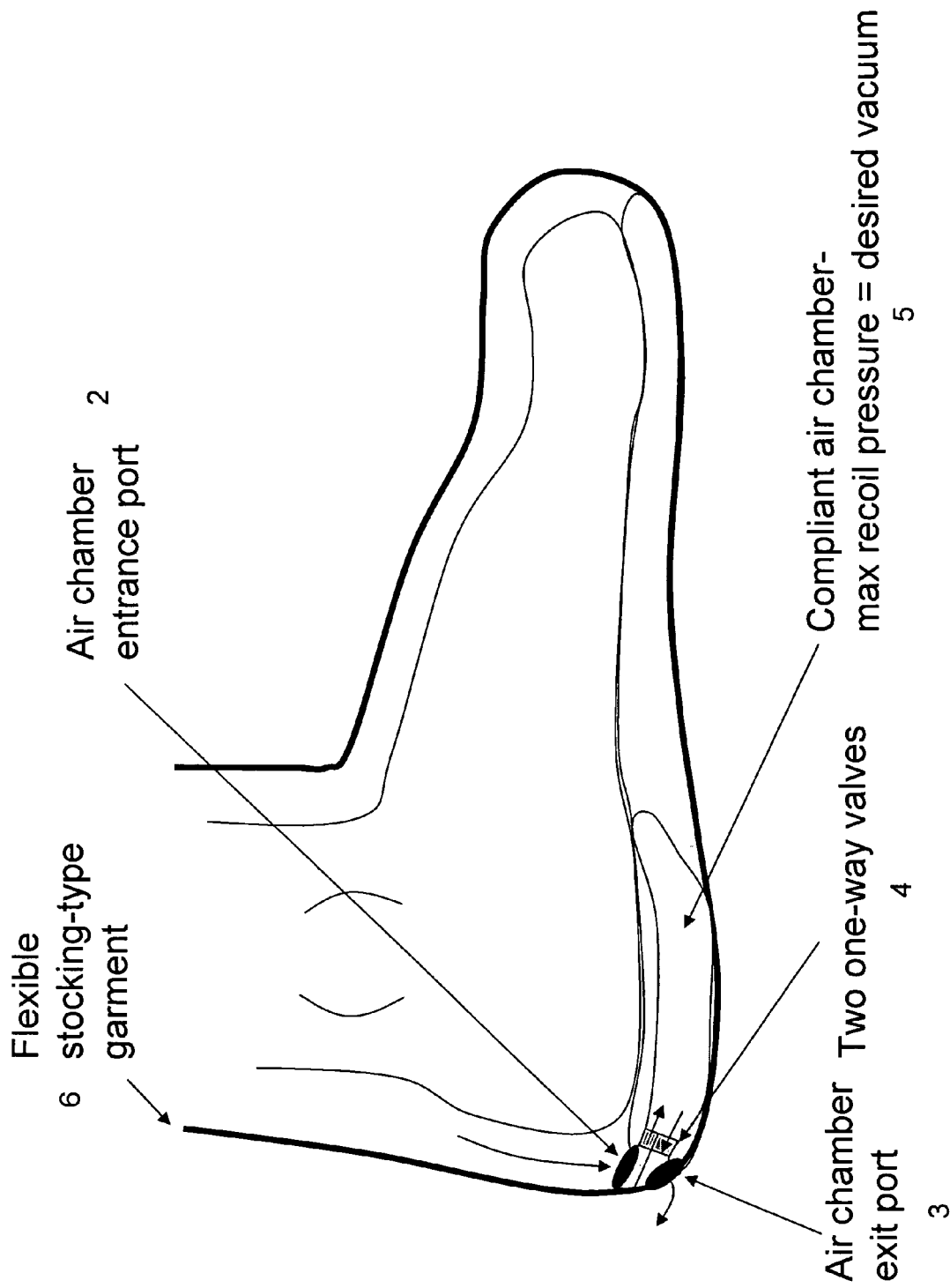
FIG. 2 is a perspective view of an expanded Dynamic Vacuum Compression Appliance illustrating the components for negative pressure generation in one embodiment of the present invention.
Figure 3:
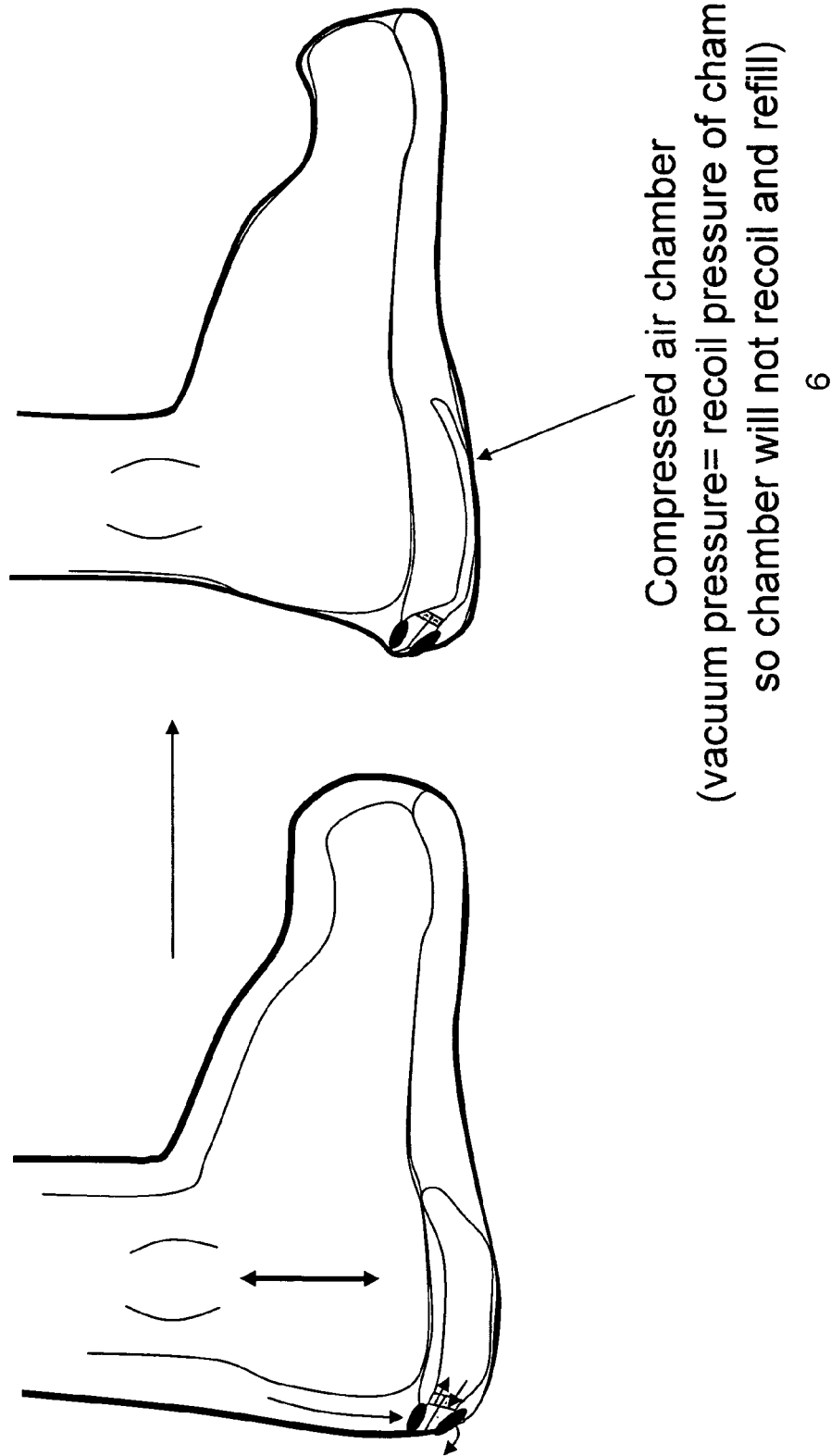
FIG. 3 is a perspective view of an expanded Dynamic Vacuum Compression Appliance illustrating the function of the air chamber in one embodiment of the present invention.

The Dynamic Vacuum Compression Appliance 1 of FIG. 1 is illustrated in greater detail in FIGS. 2 and 3. The vacuum generating mechanism is intended to be incorporated into an insole-like device designed to be placed inside of standard footwear. This component will incorporate a resilient air chamber 5 and two valves 4 or flow restrictors (such as smaller diameter tubing) to channel air out of the garment upon compression of the air chamber by the foot and to allow air to enter the air chamber from the garment with recoil of the air chamber. The recoil and compliance of the air chamber 5 can be tailored such that it will not recoil once a certain vacuum has been established, thus ensuring that the correct negative pressure is achieved 6. This appliance will thus employ the force generated during normal standing and walking to actively generate vaccum forces and allow air to be evacuated through a one-way check valve 4. An elastic or Velcro band 12 may be incorporated into the design of the device to provide a relatively airtight seal at the top of the garment to allow for vacuum generation in the leg. This generated compression will then support the superficial venous appliance, helping to reduce edema and aid venous return.

Figure 4:
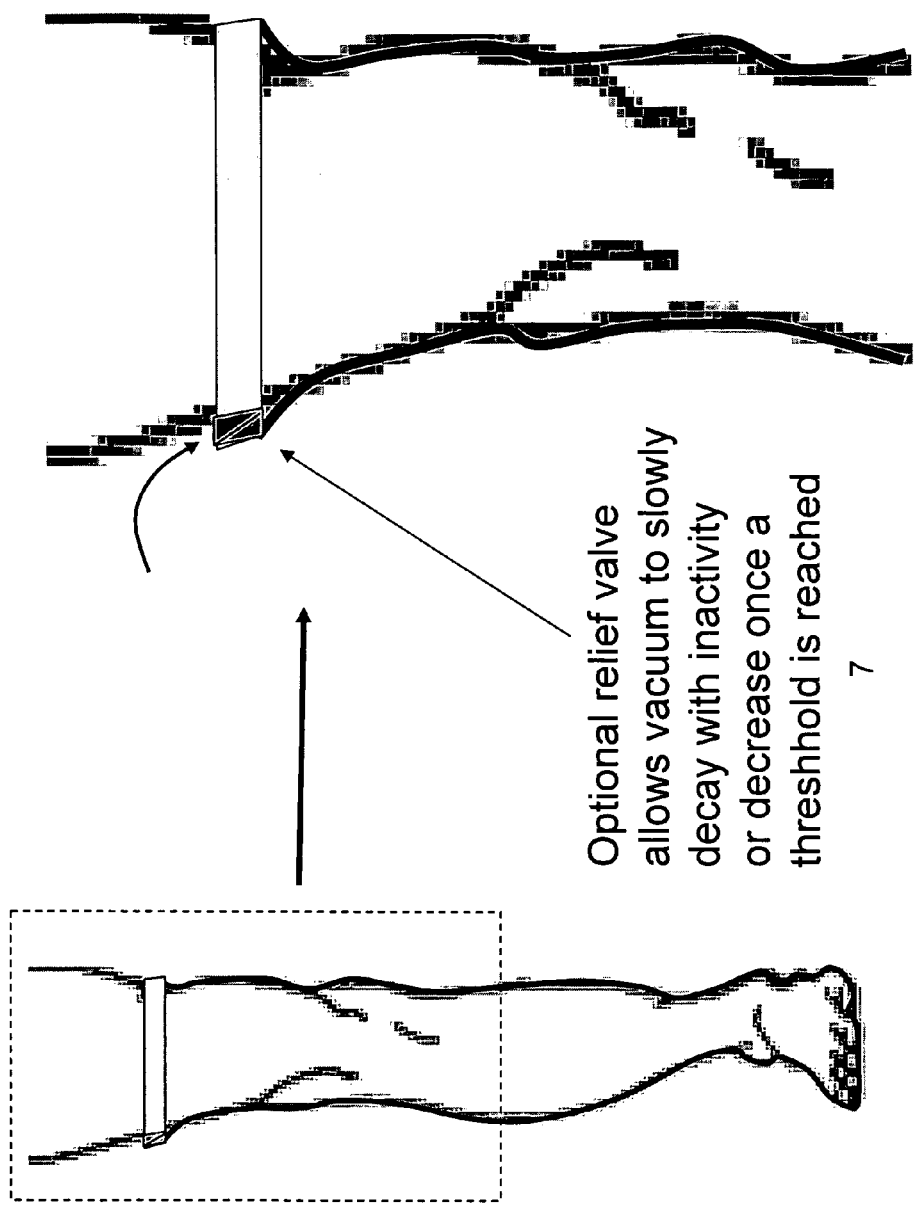
FIG. 4 is a perspective view of an expanded Dynamic Vacuum Compression Appliance with illustration of optional relief valve allows vacuum to slowly decay with inactivity or decrease once a threshold is reached.

According to one embodiment illustrated in FIG. 4, the Dynamic Vacuum Compression Appliance incorporates an optional relief valve 7 allows vacuum to slowly decay with inactivity or decrease once a threshold is reached. In this embodiment, the garment will form a partial seal such that with frequent compression of the vacuum will provide strong suction that will gradually subside once the frequency of pump application is reduced. This partial seal could also be used to ensure that the vacuum generated at the top of the garment is less than that generated at the inferior portions, thus "milking" the leg.

Figure 5:
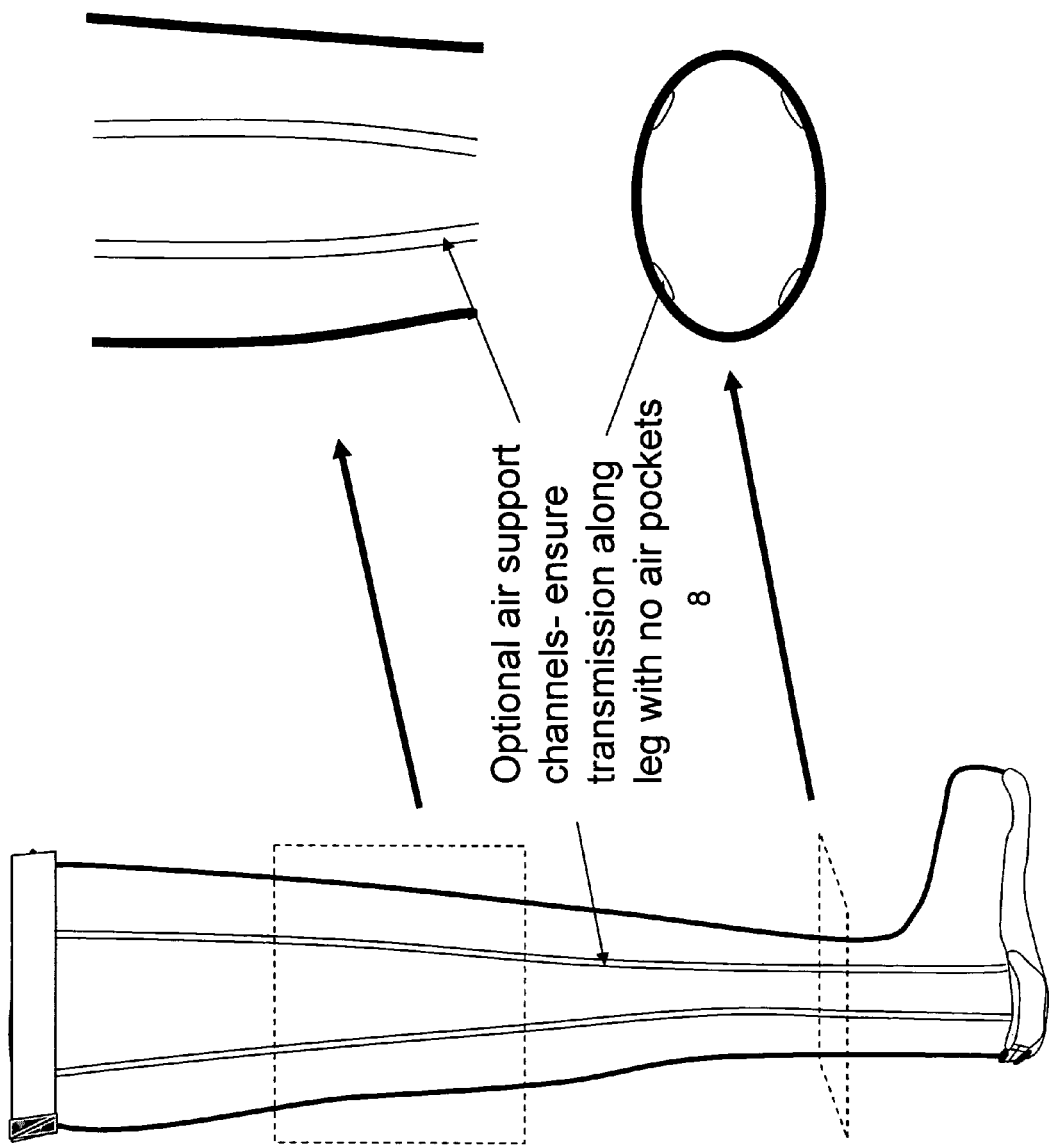
FIG. 5 is a perspective view of an expanded Dynamic Vacuum Compression Appliance with illustration of optional air support channels to ensure transmission along leg with no air pockets.
Figure 6:
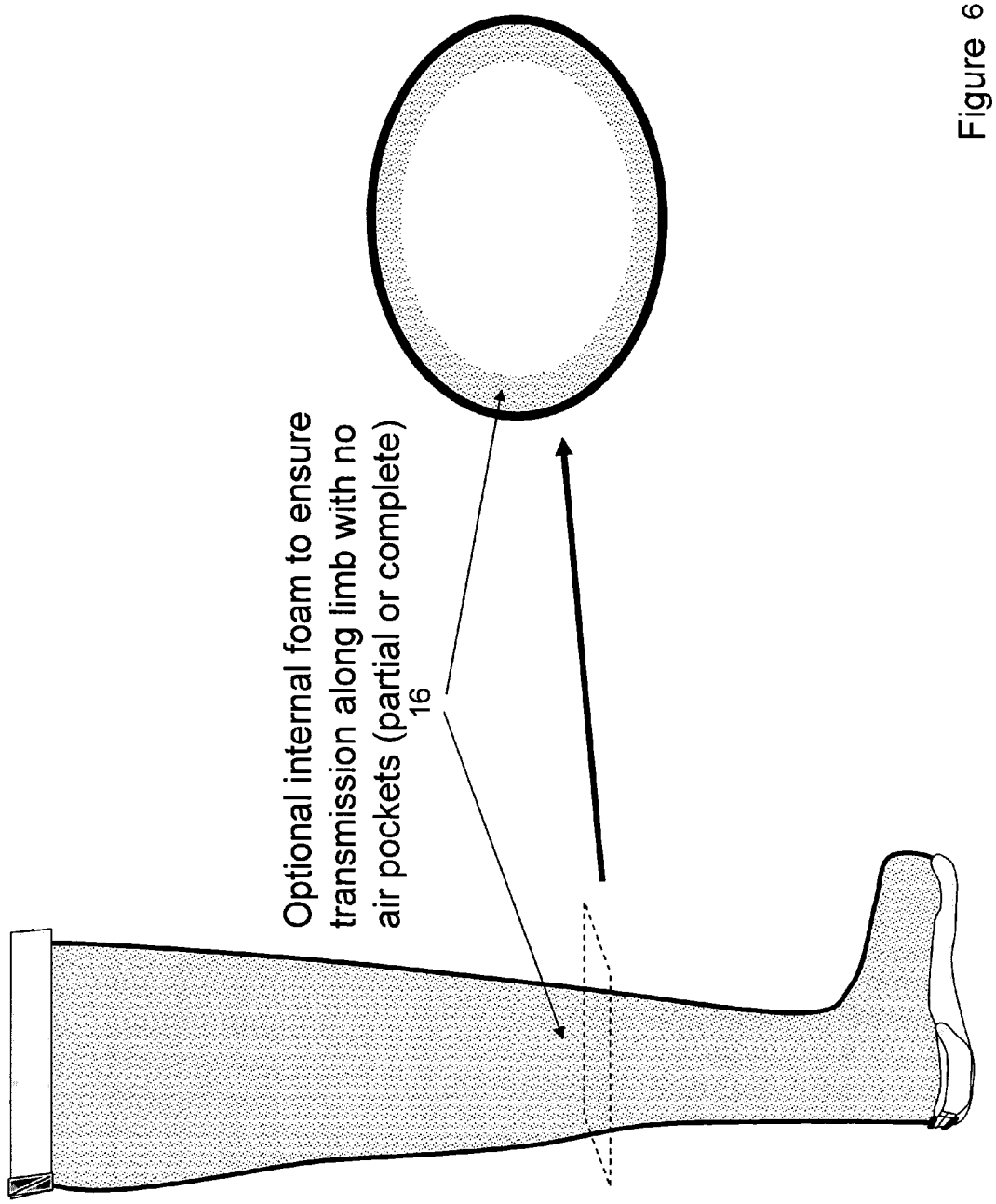
FIG. 6 is a perspective view of an expanded Dynamic Vacuum Compression Appliance with illustration of optional internal foam component to ensure transmission of vacuum along the leg with no air pockets.

According to one embodiment illustrated in FIG. 5, the Dynamic Vacuum Compression Appliance incorporates optional air support channels 8 to ensure transmission along leg with no air pockets. In this embodiment, the longitudinal air support channels 8 would allow for the transmission of vacuum from the vacuum pump to the top of the garment in a reliable manner avoiding air pockets. These channels may also be formed through the incorporation of a thin, porous internal layer to allow for transmission of vacuum over large distances. This layer of foam may be incorporated into the garment, as illustrated in FIG. 6 or applied separately.

Figure 7:
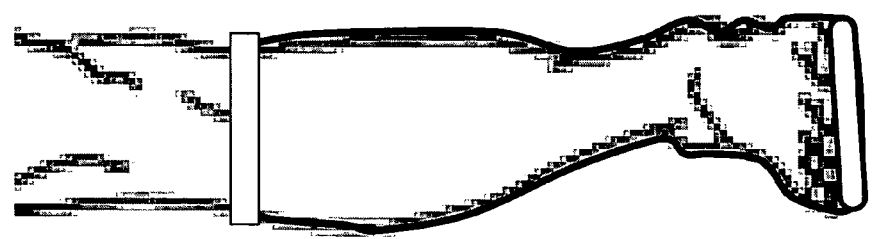
FIG. 7 is a perspective view of a Dynamic Vacuum Compression Appliance configured in accordance with one embodiment (a calf-only embodiment) of the present invention.

According to one embodiment illustrated in FIG. 7, the Dynamic Vacuum Compression Appliance is shown in a calf-only embodiment 9 as an alternative to the thigh-high embodiments shown in FIGS. 1-6. The device may also be provided in an ankle-high and even partial-foot embodiment with the only prerequisite being that of circumferential application.

Figure 8:
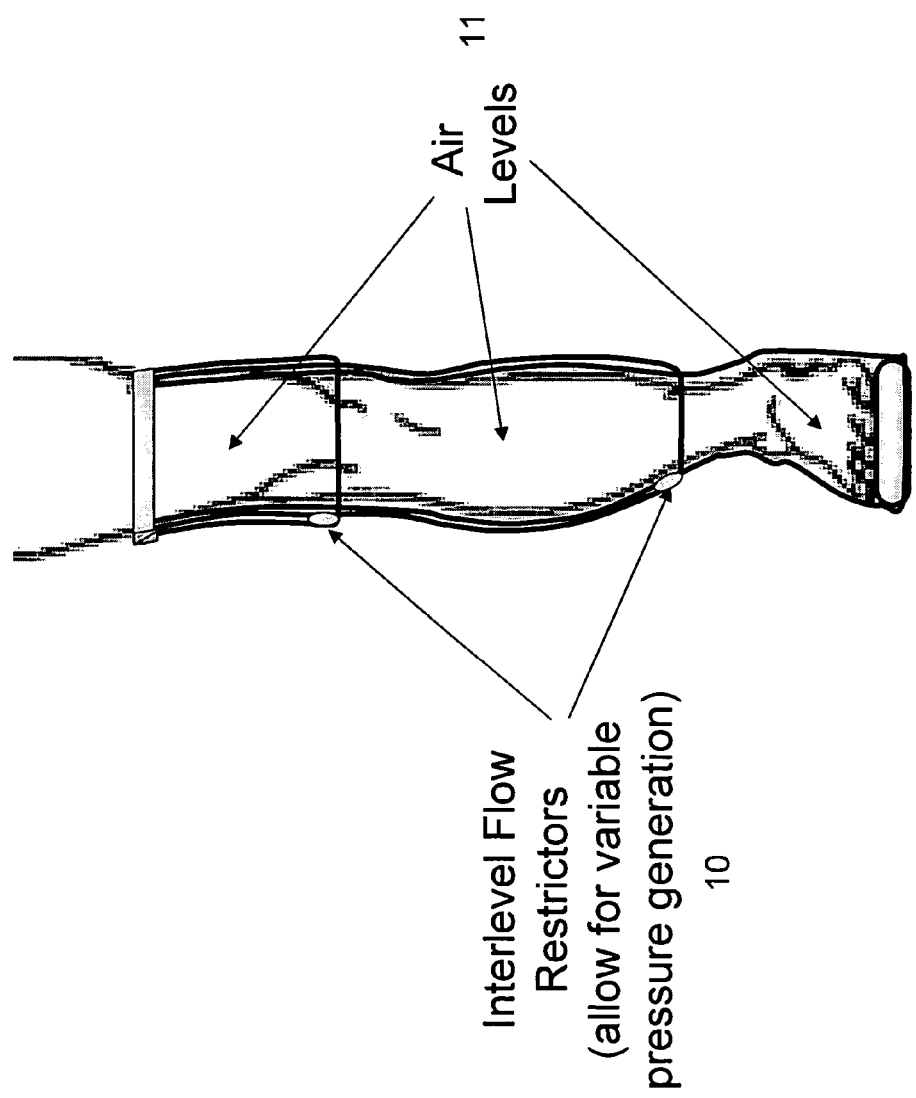
FIG. 8 is a perspective view of an expanded Dynamic Vacuum Compression Appliance illustrating the components interlevel Flow Restrictors for the allowance of variable pressure generation.

According to one embodiment illustrated in FIG. 8, the Dynamic Vacuum Compression Appliance incorporates optional interlevel flow restrictors to allow for variable pressure generation. These air levels can provide air pockets with variable access to vacuum, either using pressure-sensitive valves or simple smaller diameter higher resistance tubing such that the vacuum provided at increasing elevation is less than that in the inferior air level. This interlevel flow restriction feature will allow for the "milking of the leg" with activation of the vacuum pump. The air levels can also be used in combination with the air influx valve to provide a dynamic pressure gradient throughout the limb.

Figure 9:
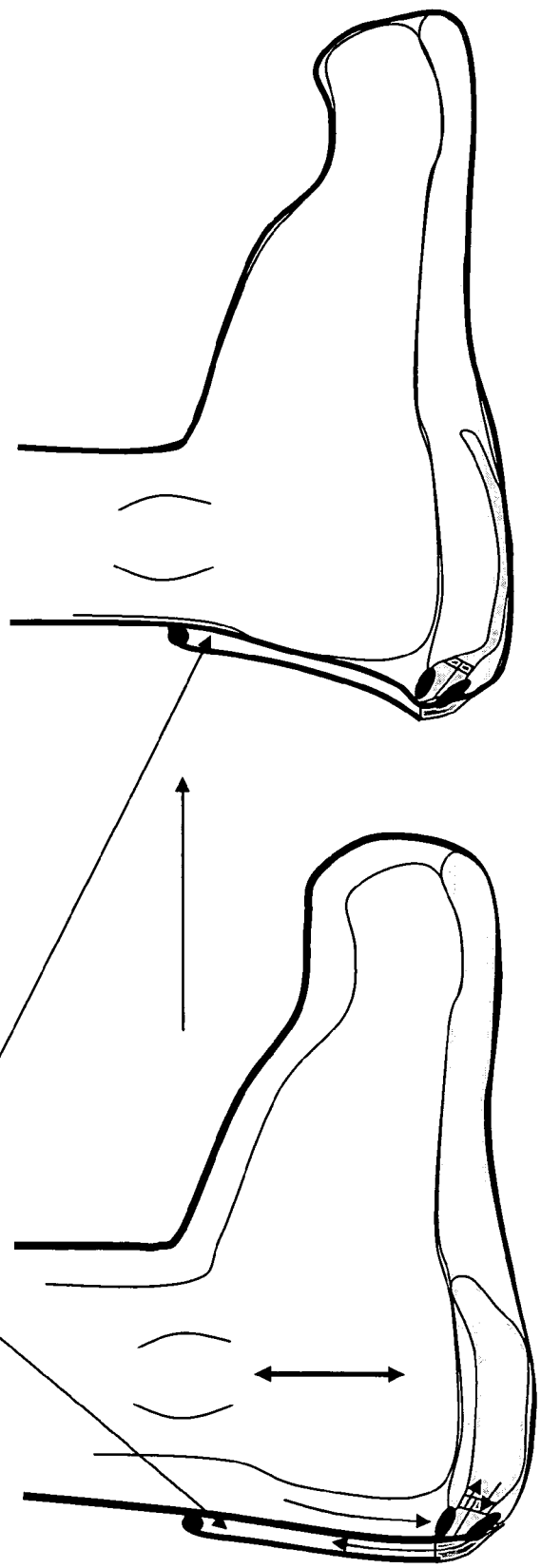
FIGS. 9 and 10 are a perspective view of the Dynamic Vacuum Compression Appliance with the fluid reservoir shown with its ability to be interchanged or emptied.
Figure 10:
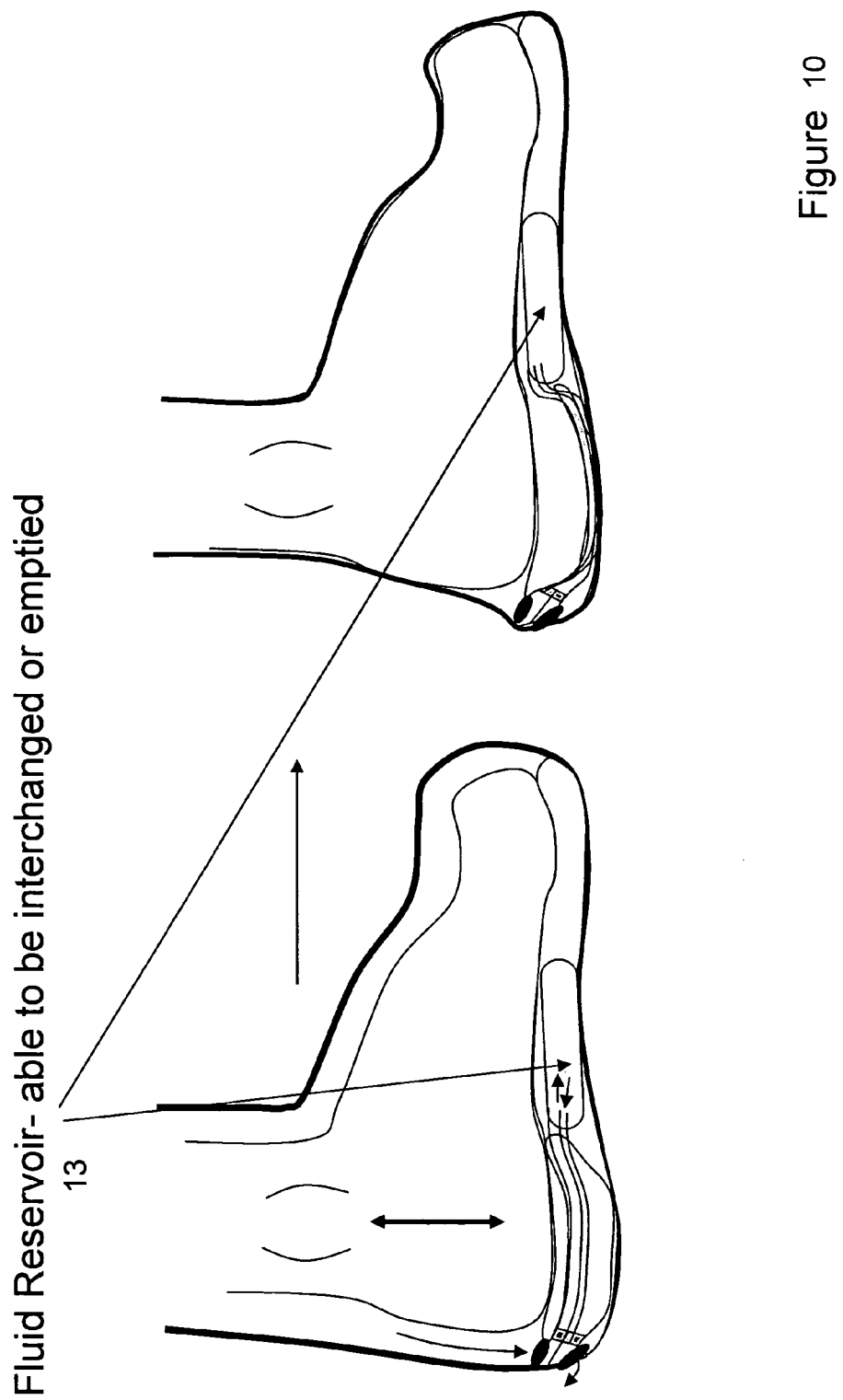

According to one embodiment illustrated in FIGS. 9 and 10, the Appliance incorporates a reservoir in line with the air chamber exit port. This reservoir would serve the purpose of holding fluid pumped out of the space around the limb with the vacuum negative pressure generation. The capability to pump fluid out of the space around the limb and contain it with the reservoir will allow the device to facilitate the healing of wounds and wound prevention.

Figure 11:
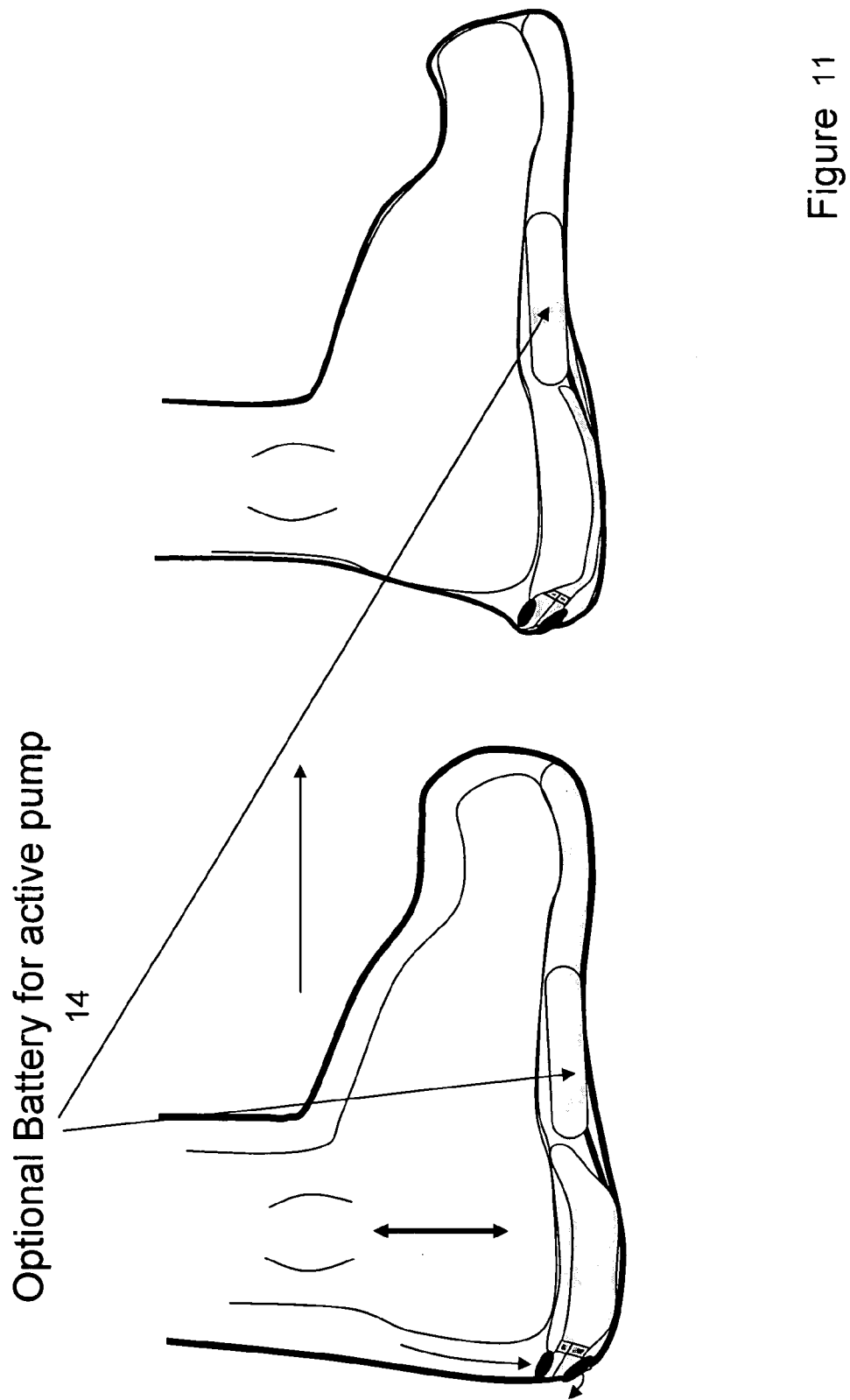
FIG. 11 is a perspective view of the Dynamic Vacuum Compression Appliance with the optional battery for an embodiment with an active pump.

According to one embodiment illustrated in FIG. 11, the Dynamic Vacuum Compression Appliance incorporates a power source (e.g. battery or other portable systems) to help generate initial negative pressure or to maintain negative pressure within the stocking type garment. This power source could be used either as a supplement to self-powered vacuum generation or instead of self-powered generation in persons that may not be ambulatory to a degree necessary to maintain and generate the appropriate negative pressure. In this or other embodiments the garment may be initially subjected to vacuum to remove any air present in the garment after initial application.

Figure 12:
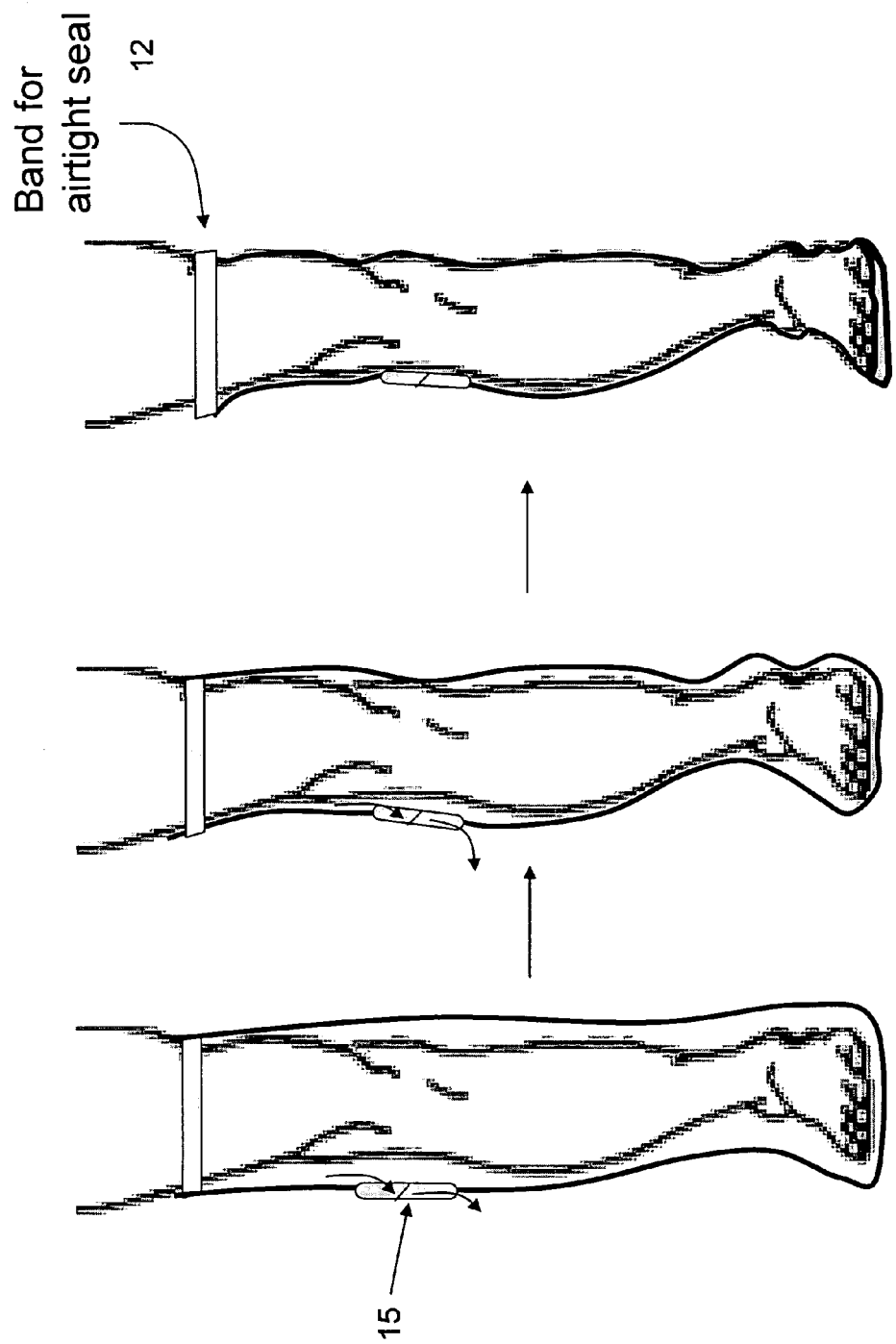
FIG. 12 is a perspective view of the pump that utilizes flexion/extension to generate vacuum (the pump itself is labeled number 15)

According to one embodiment illustrated in FIG. 12, the Dynamic Vacuum Compression Appliance incorporates a pumping mechanism that utilizes any motion of the body (e.g. flexion/extension of a joint) to generate the vacuum compression.

Figure 13:
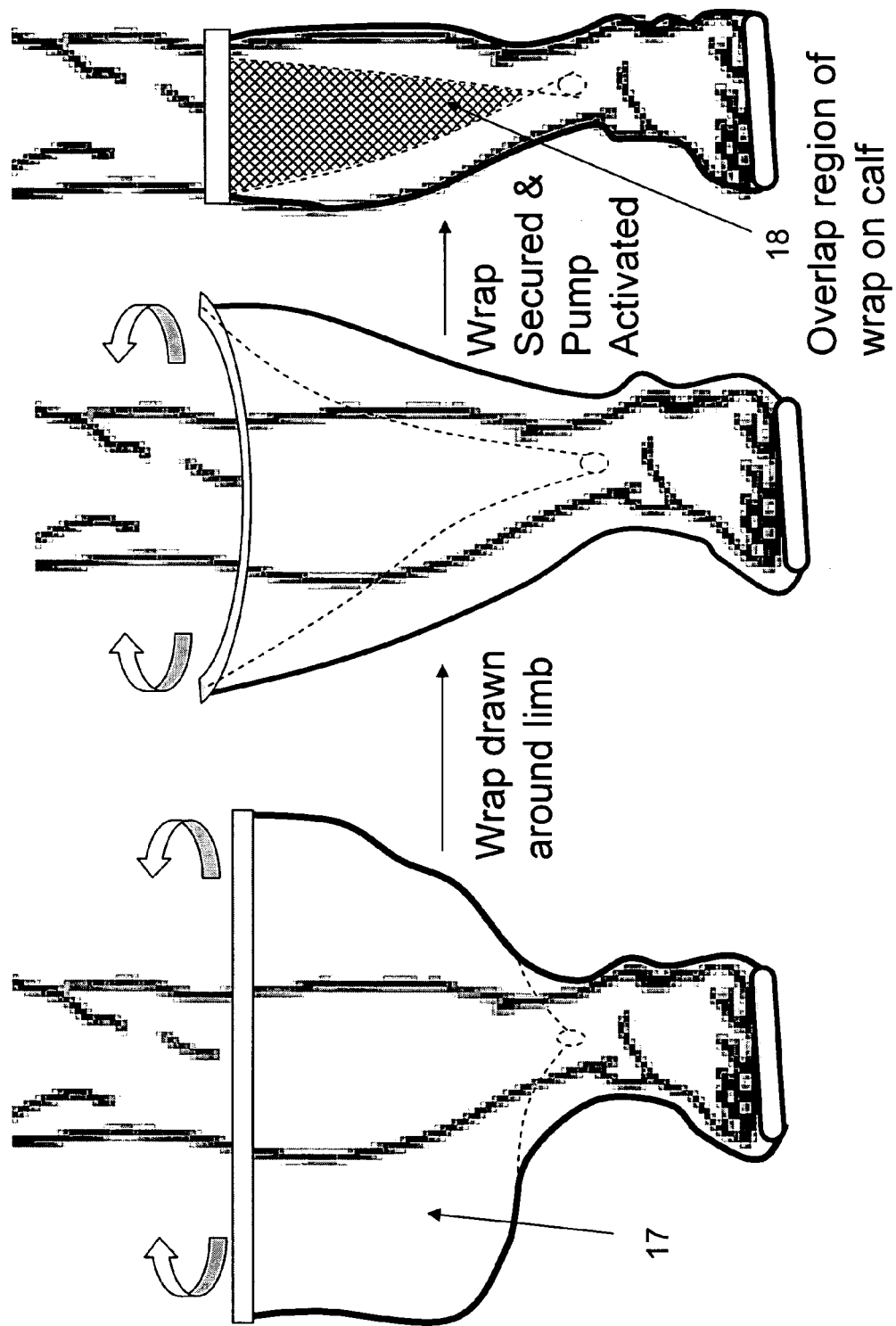
FIG. 13 is a perspective view of the Dynamic Vacuum Compression Appliance in which the flexible garment may be reversibly opened and closed to form an airtight seal allowing for increased ease of application

According to one embodiment illustrated in FIG. 13, the desired circumferential orientation can be achieved through wrapping the stocking portion of the device around the treatment area. In this manner, the stocking can sized to fit multiple patients and may be more easily applied. The stocking may also have a binding region where it is able to attach to itself to ensure a snug fit. This embodiment may be utilized in any region of the body and may be of any length and width.

Figure 14:
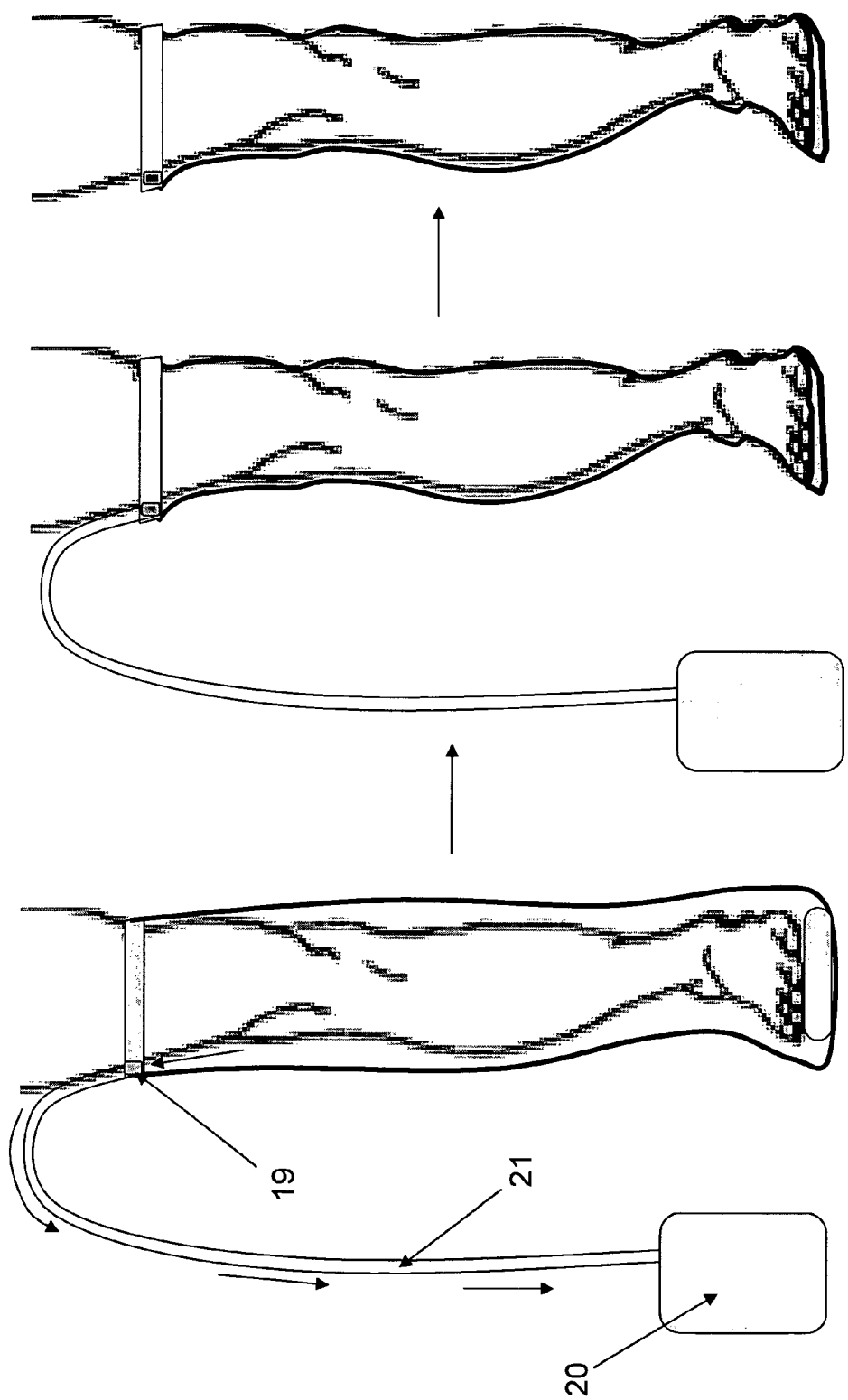
FIG. 14 is a perspective view of one embodiment of the device in which an external pump may be applied to generate vacuum in the circumferential wrap

According to one embodiment illustrated in FIG. 14, the device may employ an external pump 20 to provide vacuum in the circumferentially applied stocking. This may be the case for lower or upper extremity application. This external pump 20 may be connected to the stocking through a port 19. This port 19 is capable of opening to allow vacuum from the external pump 20 and capable of forming a partial or full air seal upon disconnection of the tubing 21. The external pump 20 may be used continuously, intermittently or during prescribed periods, ie at night while ambulation cannot power the vacuum. The external pump 20 may be used only for the evacuation of air from the stocking immediately after application. Furthermore, the external pump 20 may be the only source of vacuum, or it may be one of multiple vacuum sources including the self-powered pump illustrated in FIG. 2. In this scenario, the self-powered pump may maintain vacuum during ambulation with the external pump 20 providing vacuum during periods when the user is not ambulatory.

According to one embodiment in FIG. 15, the device may employ a single valve 22 and utilize the natural pattern of plantar compression to milk the air from the elongated resilient air chamber 23 beneath the foot. In this embodiment, there is only need for one valve 22 and one air intake port 24. Alternatively, the device may employ no valves and simply have air intake ports 24 at the heel and toe of the garment and the resilient air chamber 23 on the plantar surface.

In any embodiment, with two, one or no valves, the standard or elongated resilient air chamber may be incorporated into footwear wherein the flexible garment is capable of engaging said footwear and the flexible garment is disposable while the pumping mechanism is reusable through its permanent incorporation into footwear.

According to one embodiment, the Dynamic Vacuum Compression Appliance incorporates a tube that serves as an interface between the compliant air chamber and the flexible stocking-type garment. The tube will serve as a conduit through which air would be drawn into the compliant air chamber. In this embodiment, the tube interface could potentially pass either on the inside or on the outside of footwear. In this way, the tube interface could potentially facilitate accommodation of the compliant air chamber within footwear.

According to one embodiment, the Dynamic Vacuum Compression Appliance would incorporate a filter element as part of the proposed interface between the compliant air chamber and the flexible stocking-type garment. This filter element would limit the passage of tissue or other particles that could potentially clog the air chamber. This filter element would allow for the passage of fluid (as could potentially be associated with foot or leg wounds) but would limit passage of larger particulate matter.

According to one embodiment, the vacuum generating mechanism is incorporated into a boot (e.g. walking or post-surgical boot). With this embodiment, the air compliant chamber, valves, tubing, and other components could be built into the structure of the boot into which the compression garment would fit. This embodiment would facilitate the accommodation of limbs of various sizes, wounds of various types, and would obviate the need for designing special shoes to interface with the compression garment.

In any embodiment, the present invention may be utilized with all types of dressings, wound care products or garments. This may be particularly important for wounds with significant drainage to ensure that the dressings and wound care products wick the moisture away from the wound.

DETAILED DESCRIPTION OF THE PREFERRED EMBODIMENTS

Device

Dynamic Vacuum Compression Appliance

Indications for Use:
1) Limb edema, with associated causes including chronic venous insufficiency, congestive heart failure, lymphedema, and other related conditions
2) Prevention of fluid accumulation, and
3) Treatment of skin ulceration Methods for Use:
1) A patient with edema of the lower extremity, for example, will place the flexible stocking-type garment on the affected limb(s),
2) A tight seal will be formed at the proximal end of the stocking-type garment. This seal can be achieved in any number of different manners, including the placement of a band around the top of the stocking,
3) The stocking-type garment will be coupled to an insole-like device designed to be placed inside of standard footwear. This component will incorporate a resilient air chamber and two valves or flow restrictors (such as smaller diameter tubing) to channel air out of the garment upon compression of the air chamber by the foot and to allow air to enter the air chamber from the garment with recoil of the air chamber, and
4) The patient will then wear the device for normal day-to-day activities. The appliance will employ the force generated during normal standing and walking to actively generate vacuum forces and allow air to be evacuated through a one-way check valve. As the negative pressure builds within the stocking, the garment surfaces will draw in around the skin to generate compression for the application of controlled pressure to the limb. This generated compression will then support the superficial venous appliance, helping to reduce edema and aid venous return during ambulation. While the patient is not ambulating, the device may contain a connector which allows an externally powered vacuum to be applied to the garment. Alternatively, the garment itself will contain a low-profile electromechanical pump ergonomically designed to be worn within the flexible garment which may be recharged externally or powered using batteries.

What is claimed is:
1. A method of treating a wound or edema on a foot or lower body extremity, the method comprising:
disposing the foot or lower body extremity in a sock-shaped garment wrappable on the foot or lower body extremity circumferentially, the garment comprising a supple air-impermeable layer, a supple air-porous layer being disposed at least partially between the air-imper- meable layer and the foot or lower body extremity and further having a seal formed at a top of the garment removed from the foot, wherein the garment comprises a plurality of air pockets which are fluidly inter-coupled, the air-porous layer facilitating movement of the air interspaced between the foot or lower body extremity and the air-impermeable layer, the garment further comprising a wicking layer disposed at least partially between the air-impermeable layer and the foot or lower body extremity, the wicking layer wicking moisture away from the foot or lower body extremity;

fluidly coupling a pump to the garment; and actuating the pump to intermittently remove air interspaced between the garment and the foot or lower body extremity such that the garment collapses from an open shape sized for receiving the foot or lower body extremity into a collapsed shape against the foot in an air-tight manner when the interspaced air is removed such that each successive air pocket farther from the foot exerts a relatively lower pressure upon the foot and/or a portion of a leg creating a pressure gradient.

2. The method of claim 1 wherein disposing the foot or lower body extremity in the sock-shaped garment further comprises disposing a lower portion of a leg in a second portion of the garment.

3. The method of claim 2 wherein disposing the lower portion of the leg comprises wrapping longitudinal free ends of the second portion around the leg.

4. The method of claim 1 further comprising the step of providing a reservoir for receiving at least some liquid wicked from the wound or the edema.

5. The method of claim 1 further comprising the step of wrapping an air seal around a portion of the foot or of a leg, the air seal maintaining vacuum within the garment.

6. The method of claim 5 further comprising the step of disposing one or more valves near the air seal, the one or more air valves being configured for transferring air in and out of the garment.

7. The method of claim 1 wherein disposing the foot in a sock-shaped garment comprises providing the air-porous layer and the wicking layer as a single layer.

8. A device for treating a wound or edema on a foot, the device comprising:

a sock-shaped garment configured for receiving the foot, the garment comprising a supple air-impermeable layer wrappable on the foot circumferentially and further having a seal formed at a top of the garment removed from the foot, wherein the garment comprises a plurality of air pockets which are fluidly inter-coupled;

a pump fluidly coupled to the garment, the pump being configured to intermittently remove air interspaced between the garment and the foot whereby the garment is collapsible from an open shape sized for receiving the foot into a collapsed shape against the foot in an air-tight manner when the interspaced air is removed such that each successive air pocket farther from the foot exerts a relatively lower pressure upon the foot and/or a portion of a leg creating a pressure gradient;

a supple air-porous layer disposed at least partially between the air-impermeable layer and the foot, the air-porous layer being configured for facilitating movement of the air interspaced between the foot and the air-impermeable layer; and a wicking layer disposed at least partially between the air-impermeable layer and the foot, the wicking layer wicking moisture away from the foot.

9. The device of claim 8 wherein the garment further comprises a second portion configured for receiving at least a lower portion of a leg.

10. The device of claim 9 wherein the second portion comprises longitudinal free ends, and wherein the second portion is configured for receiving the lower portion of the leg by wrapping around the lower portion of the leg.

11. The device of claim 8 wherein the pump is positioned on or near a body limb.

12. The device of claim 8 wherein the pump is positioned in an orthotic or custom insole and is actuated by a body motion.

13. The device of claim 8 wherein the air-porous layer is coupled to the air-impermeable layer.

14. The device of claim 8 wherein the air-porous layer is separate from the air-impermeable layer.

15. The device of claim 8 wherein the air-porous layer and the wicking layer are provided as a single layer.

16. The device of claim 8 wherein the wicking layer is configured for draining liquid excreted from the wound or the edema.

17. The device of claim 15 further comprising a reservoir for receiving at least some of the liquid.

18. The device of claim 17 wherein the reservoir is disposed adjacent to the foot.

19. The device of claim 8 further comprising an air seal coupled to an end of the garment, the air seal being wrappable around a portion of the foot or of a leg and maintaining vacuum within the garment.

20. The device of claim 18 further comprising one or more air valves configured for transferring air in and out of the garment.

21. The device of claim 20 wherein the one or more valves are disposed in or near the air seal.

* * * * *